United States Patent [19]

Rasshofer et al.

[11] 4,350,781

[45] Sep. 21, 1982

[54] PROCESS FOR THE PREPARATION OF POLYMER PRECURSORS CONTAINING OXAZOLIN-2-ONE RINGS

[75] Inventors: Werner Rasshofer, Cologne; Gerhard Grögler, Leverkusen; Holger Meyborg, Odenthal, all of Fed. Rep. of Germany

[73] Assignee: Bayer Aktiengesellschaft, Leverkusen, Fed. Rep. of Germany

[21] Appl. No.: 286,419

[22] Filed: Jul. 24, 1981

[30] Foreign Application Priority Data

Aug. 7, 1980 [DE] Fed. Rep. of Germany ....... 3029922

[51] Int. Cl.³ .............................................. C08G 18/32
[52] U.S. Cl. ..................... 521/159; 521/163; 525/504; 528/62; 528/73; 528/117; 528/341; 528/403; 528/406
[58] Field of Search ................ 521/159, 163; 525/504; 528/62, 73, 117, 341, 403, 406

[56] References Cited

U.S. PATENT DOCUMENTS

| | | | |
|---|---|---|---|
| 3,716,520 | 2/1973 | Tomalia | 528/117 |
| 3,752,793 | 8/1973 | Arlt et al. | 260/78.5 T |
| 3,876,618 | 4/1975 | Clarke | 528/73 |
| 4,191,706 | 3/1980 | Marquis et al. | 528/73 |

OTHER PUBLICATIONS

Kinstle et al., "Synthesis and Characterization of Linear and Crosslinked AB-Type Polyurethanes", *Chem. Prop. Crosslinked Polym.*, [Proc ACS Symp.], pp. 21 through 47.

*Primary Examiner*—Maurice J. Welsh
*Attorney, Agent, or Firm*—Gene Harsh; Joseph C. Gil; Lyndanne M. Whalen

[57] ABSTRACT

A polymer precursor containing an oxazolin-2-one ring is made by reacting (a) an amino-reactive group containing compound having at least two groups capable of entering into an addition or condensation reaction with primary or secondary aromatically-bound amino groups with (b) an aromatic amine having at least one primary or secondary aromatically-bound amino group and at least one condensed oxazolin-2-one ring. The reactants are used in quantities such that for each aromatically bound primary or secondary amino group there are from 0.95 to 5 groups present in the amino-reactive group containing compound which are capable of reacting with the amino group. These polymer precursors may be used to produce high molecular weight polymers useful in the production of solid molded products, adhesives, foam plastics and coatings.

11 Claims, No Drawings

PROCESS FOR THE PREPARATION OF POLYMER PRECURSORS CONTAINING OXAZOLIN-2-ONE RINGS

FIELD OF THE INVENTION

This invention relates to a process for the preparation of polymer precursors containing oxazolin-2-one rings. Amines having at least one condensed oxazolin-2-one ring are reacted with polymer precursors which have groups capable of entering into an addition or condensation reaction with aromatic amino groups.

SUMMARY OF THE INVENTION

It is an object of the present invention to provide a process for the preparation of a polymer precursor having an oxazolin-2-one ring.

It is another object of the present invention to provide a process for the preparation of a polymer precursor having an oxazolin-2-one ring which precursor may be used to produce polymers suitable for the production of solid molded products, adhesives, foam plastics or coatings.

These and other objects which will be apparent to those skilled in the art are accomplished by reacting an amino-reactive group containing compound with an aromatic amine having at least one condensed oxazolin-2-one ring to form a polymer precursor containing an oxazolin-2-one ring. The amino-reactive group containing compound must have at least two groups capable of entering into an addition or condensation reaction with primary or secondary aromatically-bound amino groups. The aromatic amine must have at least one primary or secondary aromatically-bound amino group and at least one condensed oxazolin-2-one ring. The reactant materials are used in quantities such that for each aromatically bound primary or secondary amino group there are from 0.95 to 5 groups capable of reacting with the amino group.

DETAILED DESCRIPTION OF THE INVENTION

The present invention relates to a process for the preparation of polymer precursors containing oxazolin-2-one rings. These precursors react to form high molecular weight polymers when exposed to heat. These oxazolin-2-one ring-containing polymer precursors are made by reacting (a) an amino-reactive group containing compound having at least two groups capable of undergoing an addition or condensation reaction with primary or secondary aromatically-bound amino groups and (b) aromatic amines which have at least one primary or secondary aromatically-bound amino group and contain at least one condensed oxazolin-2-one ring. The reactants are used in amounts such that for each aromatically-bound primary or secondary amino group from 0.95 to 5 groups reactive with amino groups are present in compound (a). The polymer precursors containing oxazolin-2-one rings thus obtained yield high molecular weight polymers when subjected to a heat treatment at temperatures of from 100° to 200° C. This heat treatment may be carried out in the presence of compounds having at least two groups capable of entering into an addition or condensation reaction with oxazolin-2-one rings.

The aromatic amines suitable to the practice of the present invention include any aromatic amines which (i) have at least one aromatically bound, primary or secondary amino group; (ii) have at least one condensed oxazolin-2-one ring; and (iii) are otherwise inert under the reaction conditions of the process according to the present invention.

The aromatic amines having condensed oxazolin-2-one rings which may be used in the process according to the present invention preferably correspond to the general formula:

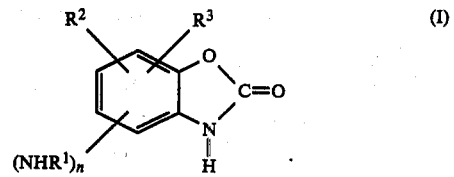

wherein
R$^1$ represents hydrogen or an aliphatic hydrocarbon group having from 1 to 4 carbon atoms;
R$^2$ and R$^3$ (which may be the same or different) represent hydrogen; an aliphatic hydrocarbon group having from 1 to 4 carbon atoms; chlorine; or when taken together, a condensed benzene ring optionally substituted by an amino group —NHR$^1$; or
R$^2$ may be as defined above, while R$^3$ may represent a group corresponding to the general formula:

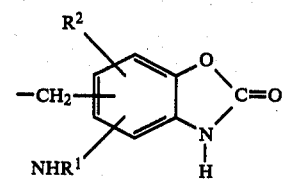

wherein
R$^1$ and R$^2$ are as defined above, and
n represents 1, or in the case of an amino-substituted condensed aromatic ring, it may also represent 0.

Compounds corresponding to the above general formula (I) in which
R$^1$ represents hydrogen;
R$^2$ and R$^3$ which may be the same or different, represent hydrogen, an aliphatic hydrocarbon group having from 1 to 4 carbon atoms or chlorine (most preferably hydrogen); and
n represents 1
are particularly preferred materials.

Typical examples of such aromatic amines having a condensed oxazolin-2-one ring include: 4-aminobenzoxazolin-2-one, 5-aminobenzoxazolin-2-one, 6-aminobenzoxazolin-2-one, 7-aminobenzoxazolin-2-one, 4-amino-6-methylbenzoxazolin-2-one, 5-amino-6-methyl-benzoxazolin-2-one, 5-amino-6-chlorobenzoxazolin-2-one, 9-aminobenzo(g)benzoxazolin-2-one, 5-aminobenzo(g)benzoxazolin-2-one, 4-aminobenzo(e)benzoxazolin-2-one, 8-aminobenzo(f)benzoxazolin-2-one, 10-aminonaphthaleno-(g)benzoxazolin-2-one, bis(4-aminobenzoxazolin-2-one-6-yl)methane, bis(5-aminobenzoxazolin-2-one-6-yl)methane, bis(7-aminobenzoxazolin-2-one-6-yl)-methane, bis(4-aminobenzoxazolin-2-one-5-yl)methane, bis(6-aminobenzoxazolin-2-one-5-yl)-methane, bis(7-aminobenzoxazolin-2-one-5-yl)-methane, bis(4-aminobenzoxazolin-2-one-6-yl)-propane, bis(4-aminobenzoxazolin-2-one-6-yl)-propane, bis(5- aminobenzoxazolin-2-one-6-yl)-ether, bis(7-aminobenzoxazolin-2-one-5-yl)-ether, bis(6-aminobenzoxazolin-2-one-5-yl)-sulphide or bis(4-aminobenzoxazolin-2-one-5-yl)-sulphone.

The secondary amines corresponding to the above-listed primary amines (wherein $R_1$ represents $C_1$–$C_4$ alkyl groups) may also be used in the process according to the present invention, although primary amines are preferred.

The aromatic amines suitable to the practice of the present invention which correspond to general formula (I) in which $R^2$ and $R^3$ represents hydrogen, a $C_1$–$C_4$ alkyl group or chlorine, may be prepared as described by J. Sam and J. L. Valentine in J. Pharm. Sci. 58, 1043 et seq (1969). Those compounds corresponding to general formula (I) wherein $R^2$ and $R^3$ represent a condensed (optionally amino-substituted) benzene ring may be prepared by reacting o-aminonaphthols with phosgene or urea to form a naphthalene having a condensed oxazolin-2-one ring, which naphthalene may then be converted by nitration and subsequent reduction of the nitro group to a compound corresponding to formula (I). Compounds corresponding to the general formula (I) wherein $R^3$ represents a group corresponding to the general formula:

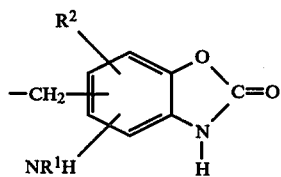

may be prepared by reactions known to those in the art. One such reaction scheme is as follows:

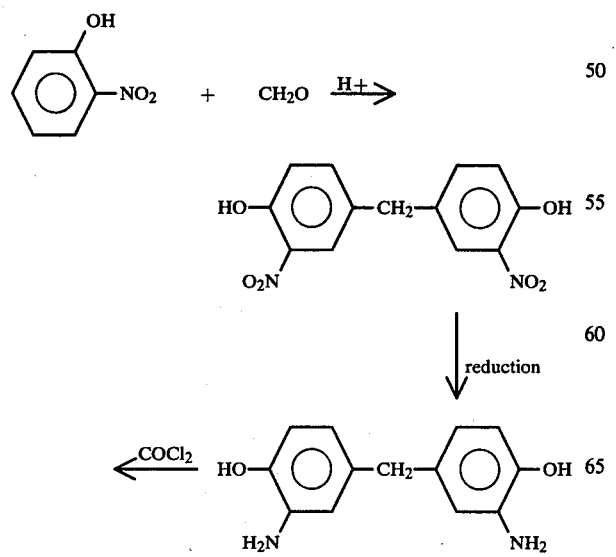

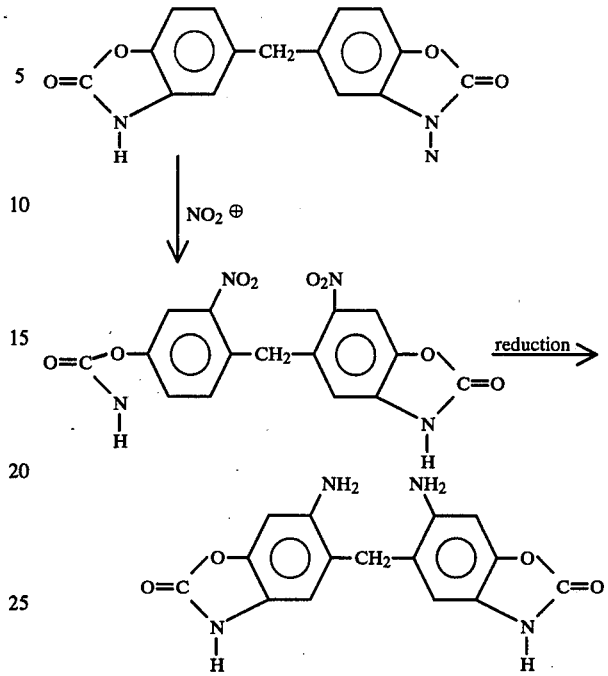

The compounds which are reacted with compounds corresponding to general formula (I) may be any organic compound containing at least two groups capable of undergoing an addition or condensation reaction with primary or secondary aromatic amino groups. Suitable amino-reactive group containing compounds of this type include organic polyisocyanates, polyepoxides and carboxylic acid derivatives.

Organic polyisocyanates which may be used in the practice of the present invention include aliphatic, cycloaliphatic, araliphatic, aromatic and heterocyclic polyisocyanates, such as those described e.g. by W. Siefken in Justus Liebigs Annalen der Chemie, 562, pages 75 to 136. Such polyisocyanates correspond to the general formula:

$$Q(NCO)_n$$

wherein
n=2–4 (preferably 2); and
Q represents an aliphatic hydrocarbon group having from 2 to 18 (preferably from 6 to 10) carbon atoms; a cycloaliphatic hydrocarbon group having from 4 to 15 (preferably from 5 to 10) carbon atoms; an aromatic hydrocarbon group having from 6 to 15 (preferably 6 to 13) carbon atoms; or an araliphatic hydrocarbon group having from 8 to 15 (preferably from 8 to 13) carbon atoms.

Examples of suitable polyisocyanates are: 1,6-hexamethylene diisocyanate; 1,12-dodecanediisocyanate; cyclobutane-1,3-diisocyanate; cyclohexane-1,3- and -1,4-diisocyanate and mixtures of these isomers; 1-isocyanato-3,3,5-trimethyl-5-isocyanatomethyl-cyclohexane (German Auslegeschrift No. 1,202,785, U.S. Pat. No. 3,401,190); 2,4- and 2,6-hexahydrotolylene diisocyanate and mixtures of these isomers; perhydro-2,4'- and/or -4,4'-diphenylmethane-diisocyanate; 1,3- and 1,4- phenylenediisocyanate; 2,4- and 2,6-tolylene diisocyanate and mixtures of these isomers; diphenylmethane-2,4'- and/or -4,4'-diisocyanate; and naphthylene-1,5-diisocyanate. Other polyisocyanates which may be used in the practice of the present invention include: polyphenyl-polymethylene polyisocyanates obtainable by aniline/formaldehyde condensation and subsequent phosgenation, (See e.g. British Pat. Nos. 874,430 and 848,671; polyisocyanates having allophanate groups (See e.g. British Pat. No. 994,890, Belgian Pat. No. 761,626 and Netherlands Patent Application No. 7,102,524); and polyisocyanates having isocyanurate groups (See e.g. in U.S. Pat. No. 3,001,973, German Pat. Nos. 1,022,789; 1,022,067; and 1,027,394 and German Offenlegungsschrift Nos. 1,929,034 and 2,004,048).

Particularly preferred organic polyisocyanates in the practice of the present invention are prepolymers having free isocyanate groups. Such prepolymers may be obtained by reacting simple organic polyisocyanates such as those described above with less than equivalent quantities of organic polyhydroxyl compounds having molecular weights of from 400 to 10,000. These isocyanate prepolymers generally have an isocyanate content of from 0.5 to 26 wt. %, preferably from 1 to 15 wt. %.

Polyhydric alcohols which may be used in the preparation of the above-described isocyanate prepolymers include the polyether and polyester polyols known to those in the art which have a molecular weight of from 400 to 10,000, preferably those having molecular weights of from 500 to 8000, and most preferably from 1000 to 6000. Suitable polyether and polyester polyols generally have from 2 to 8, preferably 2 to 4, and more preferably 2, alcoholic hydroxyl groups.

Hydroxyl polyesters which may be used in making prepolymers having free isocyanate groups include: the reaction products of polyhydric (preferably dihydric) alcohols (optionally with the addition of trihydric alcohols) and polybasic (preferably dibasic) carboxylic acids. In addition to the free polycarboxylic acids, the corresponding polycarboxylic acid anhydrides, polycarboxylic acid esters of lower alcohols and mixtures thereof may also be used to make hydroxyl polyesters suitable to practice of the present invention. These polycarboxylic acid compounds may be aliphatic, cycloaliphatic, aromatic and/or heterocyclic. They may also be substituted (e.g. with halogen atoms) and/or unsaturated. Examples of such carboxylic acids and derivatives are: succinic acid, adipic acid, suberic acid, azelaic acid, sebacic acid, phthalic acid, isophthalic acid, trimellitic acid, phthalic acid anhydride, tetrahydrophthalic acid anhydride, hexahydrophthalic acid anhydride, tetrachlorophthalic acid anhydride, endomethylene tetrahydrophthalic acid anhydride, glutaric acid anhydride, maleic acid, maleic acid anhydride, fumaric acid, dimerized and trimerized unsaturated fatty acids (optionally mixed with monomeric unsaturated fatty acids such as oleic acids), dimethylterephthalate and terephthalic acid-bis-glycol esters. Suitable polyhydric alcohols which may be reacted with these carboxylic acids to form hydroxyl polyesters include: ethylene glycol, (1,2)- and (1,3)- propylene glycol, (1,4)- and (2,3)- butylene glycol, (1,6)- hexane diol, (1,8)-octane diol, neopentylglycol, 1,4-bis-hydroxymethylcyclohexane, 2-methyl-1,3-propane diol, glycerol, trimethylolpropane, (1,2,6)- hexane triol, (1,2,4)-butane triol, trimethylolethane, pentaerythritol, quinitol, mannitol, sorbitol, formitol, methyl glycoside, diethylene glycol, triethylene glycol, tetraethyleneglycol and higher polyethylene glycols, dipropylene glycol and higher polypropylene glycols, and dibutylene glycol and higher polybutylene glycols. The polyesters prepared from the above-described carboxylic acids and polyhydric alcohols may contain a proportion of carboxyl end groups. Polyesters of lactone such as ε-caprolactone, or of hydroxycarboxylic acids, such as ω-hydroxycaproic acid may also be used in making the prepolymers having free isocyanate groups suitable to the practice of the present invention.

Suitable polyether polyols for the preparation of the isocyanate prepolymers are also known. Such polyether polyols may be prepared, for example, by the polymerization of epoxides alone or in the presence of Lewis catalysts.

Appropriate epoxides are ethylene oxide, propylene oxide, butylene oxide, tetrahydrofuran, styrene oxide and epichlorohydrin. $BF_3$ is an example of a suitable Lewis catalyst. Polyether polyols may also be prepared by chemical addition of epoxides such as those enumerated above (preferably of ethylene oxide and propylene oxide) to starting compounds having reactive hydrogen atoms. Typical examples of active hydrogen containing compounds are: water, ammonia, alcohols and amines. Specific examples of these compounds are ethylene glycol, (1,3)-propylene glycol, trimethylolpropane, glycerol, sorbitol, 4,4'-dihydroxy-diphenylpropane, aniline, ethanolamine and ethylene diamine. Sucrose polyethers (See e.g. in German Auslegeschrift Nos. 1,176,358 and 1,064,938) and polyethers started on formitol or formose (German Offenlegungsschrift Nos. 2,639,083 and 2,737,951) may also be used to prepare the prepolymer having free isocyanate groups useful in the practice of the present invention. It is generally preferred to use polyethers which contain predominantly primary OH groups (i.e. up to 90 wt. % based on all OH groups present in the polyether).

Typical polyesters and polyether polyols suitable to the practice of the present invention are described in High Polymers, Vol. XVI, "Polyurethanes, Chemistry and Technology" by Saunders-Frisch, Interscience Publishers, New York, London Volume I, 1962, pages 32–42 and 44–54, and Volume II, 1964, pages 5–6 and 198–199, and in Kunststoff-Handbuch, Volume VII, Vieweg-Hocktlen, Carl-Hanser-Verlag, Munich, 1966, e.g. on pages 45–71.

Mixtures of the above-mentioned polyether and polyester compounds having molecular weights of from 400 to 10,000 and containing at least two isocyanate reactive hydrogen atoms may also be used in the present invention.

Instead of or in addition to the above-mentioned relatively high molecular weight polyhydroxyl compounds, polythioethers, polyacetals, polycarbonates and polyester amides having hydroxyl end groups and polyhydroxyl compounds already containing urethane or urea groups may be used to prepare the isocyanate prepolymers of the present invention. Such compounds which are known to those in the art are however, less preferred. Simple low molecular weight polyols having molecular weights of from 62 to 400 (such as ethylene glycol, neopentyl glycol, hexamethylene glycol, glycerol and trimethylolpropane) may also be used in the preparation of the isocyanate prepolymers. Diamines known to those in the art, such as hexamethylenediamine or isophoronediamine, may also be used in subequivalent quantities for the preparation of isocyanate prepolymers. Such diamines are less preferred however.

Polyepoxides, such as glycidyl ether may also be used as the amino-reactive compound containing at least two groups capable of undergoing an addition or condensation reaction with primary or secondary amino groups. Such epoxides may be prepared by epoxidation of the corresponding allyl ethers or by known methods of reacting a molar excess of epichlorohydrin with an aromatic polyhydroxyl compound (e.g. isopropylidene bisphenol, a Novolak, resorcinol or the like). Epoxide derivatives of methylene- or isopropylidene-bisphenols are particularly preferred. In the following examples, the epoxide resin used was the diglycidyl ether of 4,4′-isopropylidene-bisphenol.

Common polyepoxides suitable to the present invention are the resinous epoxide polyethers obtained by the reaction of an epihalohydrin, (such as epichlorohydrin or the like) with a polyhydroxyphenol or a polyhydroxylalcohol. The epoxide resins contain on an average at least two reactive 1,2-epoxide groups per molecule. Examples of suitable dihydroxyphenols are: 4,4′-isopropylidene-bisphenol, 2,4′-dihydroxy-diphenyl-ethylmethane, 3,3′-dihydroxy-diphenylidethylmethane, 3,4′-dihydroxy-diphenylmethyl-propyl-methane, 2,3′-dihydroxy-diphenylethylphenyl-methane, 4,4′-dihydroxydiphenylpropylphenyl-methane, 4,4′-dihydroxy-diphenyl-butylphenyl-methane, 2,2′-dihydroxy-diphenylditolyl-methane, 4,4′-dihydroxy-diphenyltolyl-methane and the like. Other polyhydroxyphenols which may also be reacted with an epihalohydrin to produce these epoxide polyethers include compounds such as resorcinol, hydroquinone, substituted hydroquinones (e.g. methyl hydroquinone), and the like.

Polyhydroxyalcohols which may be reacted with an epihalohydrin to produce such resinous epoxide polyethers include: ethylene glycol; propylene glycols; butylene glycols; pentane diols; bis-(4-hydroxycyclohexyl)-dimethylmethane; 1,4-dimethylolbenzene; glycerol; 1,2,6-hexane triol; trimethylolpropane; mannitol; sorbitol; erythritol; pentaerythritol; dimers, trimers and higher polymers of the enumerated polyols (e.g. polyethylene glycols, polypropylene glycols, triglycerol or dipentaerythritol), polyallyl alcohols; polyhydroxythioethers, e.g. 2,2′, 3,3′-tetrahydroxydipropylsulphide; mercapto alcohols, such as monothrioglycerol or dithioglycerol; partially esterified polyhydroxy alcohols, such as monostearine or pentaerthritol monoacetate; and halogenated polyhydroxy alcohols, such as the monochlorohydrins of glycerol, sorbitol or pentaerythritol.

Another group of polymeric polyepoxides which may be used in the present invention and may be hardened by amine is the epoxide Novalak resins which may be prepared by the reaction of an epihalohydrin (such as epichlorohydrin) with the resinous condensate of an aldehyde (e.g. of formaldehyde), either with a monohydroxyphenol (such as phenol itself), or with a polyhydroxyphenol, preferably in the presence of a basic catalyst (e.g. sodium or potassium hydroxide). Further details concerning the properties and preparation of these epoxide Novalak resins may be found in Handbook of Epoxy Resins by H. Lee and K. Neville, McGraw Hill Book Co., New York, 1967.

Carboxylic acid derivatives may also be used as the amino-reactive compound containing at least two groups capable of undergoing an addition or condensation reaction with aromatic primary or secondary amino groups. Suitable carboxylic acid derivatives include: acid chlorides, esters or carboxylic acid anhydrides having at least two acid chloride, ester or anhydride groups. Specific examples of such materials are: glutaric acid dichloride, adipic acid dichloride, pimelic acid dichloride, suberic acid dichloride, azelaic acid dichloride, sebacic acid dichloride, isophthalic acid dichloride, terephthalic acid dichloride, glutaric acid dimethyl ester, adipic acid dimethyl ester, pimelic acid dimethyl ester, suberic acid dimethyl ester, azelaic acid dimethyl ester, sebacic acid dimethyl ester, isophthalic acid dimethyl ester and terephthalic acid dimethyl ester, 1,2,4,5-benzene-tetracarboxylic acid dianhydride, dicyclo/222/octane-(7)-2,3,5,6-tetracarboxylic acid anhydride, perylene-3,4,9,10-tetracarboxylic acid dianhydride or benzophenone-3,4,3′,4′-tetracarboxylic acid dianhydride. Bis-chlorocarbonic acid esters such as butane diol-1,4-bis-chlorocarbonic acid ester, hexane diol-1,6-bis-chlorocarbonic acid ester, 3-methylpentane diol-1,5-bis-chlorocarbonic acid ester or diglycol-bis-chlorocarbonic acid ester may also be used in the process according to the present invention.

The polyisocyanate prepolymers described above are preferred over the polyepoxide and carboxylic acid derivatives as the amino-reactive compound having at least two groups capable of undergoing addition or condensation reaction with a primary or secondary aromatic amino compound in the present invention.

The reactants of the process according to the present invention are used in amounts such that from 0.95 to 5 reactive groups capable of entering into an addition or condensation reaction with the amino groups are present for each primary or secondary amino group of the aromatic amine which has a condensed oxazolin-2-one ring. When organic polyisocyanates are used, the equivalent ratio of isocyanate groups to amino groups is preferably from 0.95:1 to 2.5:1. If the reactants are used in amounts such that the equivalent ratio of isocyanate groups to amino groups is from 0.95:1 to 1.5:1 (particularly from 1:1 to 1.2:1), the reaction products obtained are primarily compounds free from isocyanate groups (the excess isocyanate groups are generally used up in side reactions). The compounds thus produced have from 2 to 6 condensed oxazolin-2-one rings, depending upon the isocyanate functionality of the polyisocyanate and the quantity of oxazolin-2-one rings initially present in the aromatic amine. These end products are generally not self-cross-linking, but may be converted into high molecular weight polymers by means of suitable chain-lengthening or cross-linking agents.

If the organic polyisocyanates are used in quantities corresponding to an NCO/NH$_2$ equivalent ratio of higher than 1.5:1 (in particular from 2:1 to 2.5:1), the product obtained still contain free isocyanate groups in addition to the condensed oxazolin-2-one ring. Such reaction products are self-cross-linking upon exposure to heat due to the reactivity of the oxazoline-2-one groups with the isocyanate groups.

If the process according to the present invention is carried out using the above-described polyepoxides, the results obtained are analogous to those achieved when polyisocyanate prepolymers are used. That is, depending upon the equivalent ratio of epoxide groups to amino groups, the reaction products which contain free hydroxyl groups due to ring opening of the epoxide groups may also have excess epoxide groups in addition to the condensed oxazolin-2-one rings. Such a reaction product may or may not be self-cross-linking, depending on the excess epoxide group content.

If the process according to the present invention is carried out using acid derivatives as the amino-reactive compound, the equivalent ratio of amino group-reactive groups to amino groups should preferably be from 0.95:1 to 1.1:1 so that the reaction products obtained will not be self-cross-linking, but will be capable of being chain-lengthened or cross-linked with the aid of the chain-lengthening or cross-linking agents due to the oxazolin-2-one ring present.

The reaction temperature employed in the process of the present invention will depend upon the nature of the material used as the amino-reactive compound. If organic polyisocyanates are used, the process according to the present invention should preferably be carried out at a temperature of from 20° to 100° C., most preferably from 50° to 90° C. If polyepoxides are used, the reaction temperature should generally be from 40° to 120° C., most preferably from 70° to 100° C. If acid chlorides or anhydrides are used, the reaction temperature should generally be from 10° to 150° C., most preferably from 40° to 120° C. When carboxylic acid esters are used, the reaction temperature should preferably be from 80° to 200° C., most preferably from 100° to 160° C.

The process according to the present invention may be carried out with or without an inert solvent. Examples of suitable solvents include dioxane, tetrahydrofuran, benzene, toluene, chlorobenzene, nitrobenzene, ethylene glycol monoethyl ether, diethylene glycol dimethyl ether and ethylene glycol monomethyl ether monoacetate.

The reaction products obtained by the process of the present invention contain aromatic ring systems having condensed oxazolin-2-one rings. These oxazolin-2-one ring systems are linked through urea groups (if a polyisocyanate is used as the amino-reactive compound), secondary or tertiary amino groups (if a polyepoxide is used) or amide groups (if an acid derivative is used). The addition or condensation reaction which take place in the process according to the present invention may be illustrated by the following equation:

(a) Reactions with organic polyisocyanates:

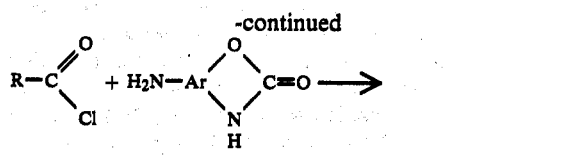

(b) Reactions with polyepoxides:

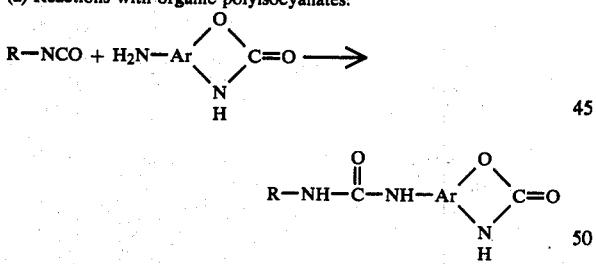

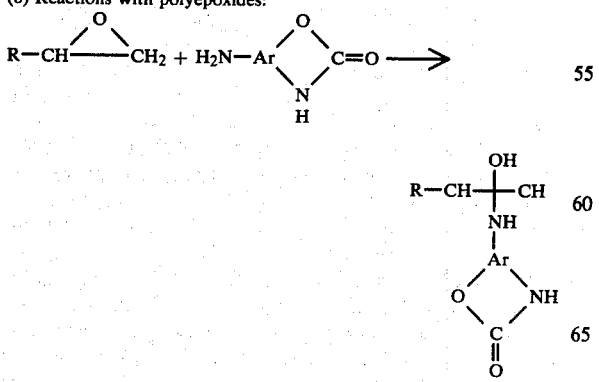

(c) Reactions with acid chlorides or esters:

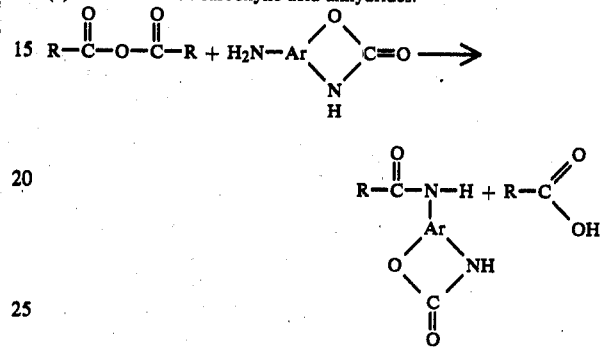

(d) Reactions with carboxylic acid anhydrides:

The condensed oxazolin-2-one rings present in the products obtained by the process according to the present invention are susceptible to further reactions. The hydrogen atom attached to the nitrogen of the oxazolin-2-one ring may react with organic isocyanates in accordance with the reaction scheme:

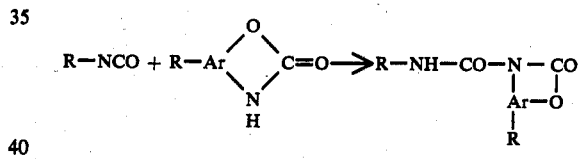

or with epoxides according to the reaction scheme:

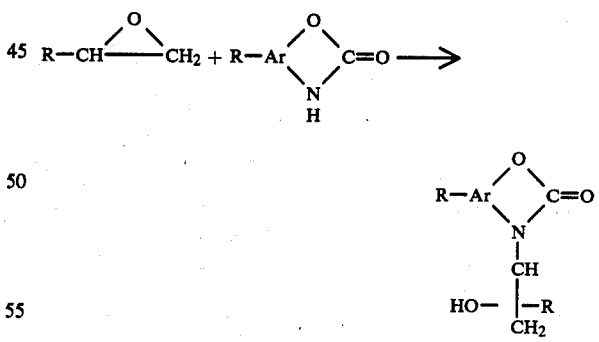

Oxazolin-2-one rings react with primary or secondary amines in accordance with the reaction scheme:

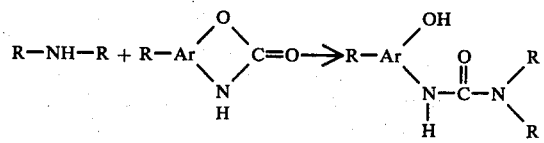

In these equations, which serve only as illustrations of the individual reaction mechanisms, the groups R and Ar represent groups which are inert in the reactions with respect to the other components present.

The products of the process of the present invention may be cross-linked or chain-lengthened with compounds such as organic polyisocyanates; polyepoxides; acid chlorides (which are at least difunctional); bis-acid anhydrides; and organic polyamines carrying primary or secondary amino groups. If the product of the present invention still contains free isocyanate groups or free epoxide groups, it is self-cross-linking or "self-chain lengthening" when exposed to heat. A cross-linking or chain-lengthening agent could, however, be added to such self-cross-linking or "self-chain-lengthening" compounds before they are cross-linked or chain-lengthened, to reinforce the cross-linking effect. Inclusion of such a cross-linking or chain-lengthening compound is frequently advisable, particularly when polyepoxides are used as the amino-reactive compound because in addition to the oxazolin-2-one rings the products still contain hydroxyl groups formed by ring opening of the epoxide groups. These hydroxyl groups are capable of reacting with isocyanate groups or epoxide groups.

Cross-linking or chain-lengthening agents appropriate to the practice of the present invention are organic polyisocyanates (described and exemplified above), particularly isocyanate prepolymers; polyepoxides such as those described and exemplified above; acid derivatives such as those described and exemplified above; and organic polyamines. Examples of suitable polyamines are: aliphatic diprimary diamines having from 2 to 12 carbon atoms; diprimary cycloaliphatic diamines having from 6 to 15 carbon atoms; diprimary aromatic diamines having from 6 to 15 carbon atoms. Specific amine compounds which may be used include: ethylene diamine, tetramethylene diamine, hexamethylene diamine, undecamethylene diamine, dodecamethylene diamine, 1-amino-3,3,5-trimethyl-5-aminomethylcyclohexane, 2,4- and 2,6- hexahydrotrolylene diamine and mixtures thereof, perhydro 2,4'- and 4,4'- diaminodiphenylmethane, p-xylylene diamine, bis-(3-aminopropyl)-methylamine, 4,4'-diamino-dicyclohexyl-methane, 3,3'-dimethyl-4,4'-diamino-dicylohexylmethane, 3,5,3',5'-tetraethyl-4,4'-diamino-dicyclohexylmethane and 2,2'-bis-(4-aminocyclohexyl)-propane. Organic polyamines obtained, for example, by hydrolysis of the isocyanate groups of the isocyanate prepolymers described above may also be used as chain-lengthening or cross-linking agents. Cycloaliphatic triamines such as those mentioned in German Offenlegungsschrift No. 2,614,244, and secondary amines, such as piperazine or N,N',N''-trimethyl-diethylenetriamine are also suitable cross-linking or chain-lengthening agents.

In addition to the chain-lenghthening and cross-linking agents exemplified above, hydrazine and hydrazne derivatives are also suitable to the practice of the present invention. Examples of suitable hydrazine derivatives include methylhydrazine; N,N'-dimethyl-hydrazine and homologues thereof; acid dihydrazides, e.g. carbodihydrazide, oxalic acid dihydrazide, the dihydrazides of malonic acid, succinic acid, glutaric acid, adipic acid or sebacic acid; semicarbazido-alkylene-hydrazides, e.g. β-semicarbazido-propionic acid hydrazide (German Offenlegungsschrift No. 1,770,591); and semicarbazido-alkylene-carbazic acid esters, e.g. 2-semicarbazido-ethyl-carbazic ester (German Offenlegungsschrift No. 1,918,504).

In the practice of the present invention, the cross-linking or chain-lengthening agents should generally be used in quantities such that from 0 to 5 (preferably from 0.95 to 1.05) reactive groups in the chain-lengthening or cross-linking agent are available for each group in the product which is reactive with the cross-linking agent (the oxazolin-2-one ring counts as a monofunctional group). The quantity of cross-linking agent used is dependent upon the quantity of isocyanate or epoxide groups present in the product of the process. It may therefore be unnecessary to use a cross-linking or chain-lengthening agent particularly if equivalent quantities of isocyanate groups and oxazolin-2-one rings are present in the product of the process.

The temperature at which the cross-linking or chain-lengthening reaction takes place depends primarily upon the nature of the cross-linking or chain-lengthening agent. In the case of organic polyisocyanates, organic polyamines, organic acid anhydrides and organic acid chlorides, the temperature should generally be from 100° to 180° C., preferably from 120° to 160° C. If at least difunctional carboxylic acid esters are used or if polyepoxides are used, the cross-linking or chain-lengthening temperature should generally be from 140° to 200° C., preferably from 150° to 180° C.

Catalysts may be used both in making the polymer precursor of the present invention and when converting the polymer precursor to a high molecular weight polymer. When the polymer precursor is prepared from organic polyisocyanates it is frequently advisable to use a tertiary amine catalyst, such as triethylene diamine or N,N-dimethyl-benzylamine. When the cross-linking or chain-lengthening reaction is carried out using organic polyamines, the reaction may be catalyzed by titanium tetraalkylates, such as titanium tetrabutylate or titanium tetraethylate.

When an organic acid chloride is used in preparing the polymer precursor of the present invention or as a cross-linking or chain-lengthening agent, it is essential that a basic material be added to the mixture to neutralize the hydrogen chloride formed in the reaction. Suitable bases for this purpose are triethylamine, tripropylamine, tributylamine, pyridine, piperidine, morpholine and piperazine.

The production of high molecular weight polymers from the polymer precursor of the present invention may be carried out either with or without suitable inert solvents.

Foam plastics may be produced from the polymer precursor of the present invention by means of appropriate blowing agents, such as azocarbonamides which give off a gas when heated. Water may also be used as blowing agent if organic polyisocyanates are used as cross-linking or chain-lengthening agents.

The mechanical properties (e.g., hardness and elasticity) of the high molecular weight polymers prepared from the polymer precursor of the present invention are dependent upon the specific starting materials used in making the polymer precursor and the specific chain-lengthening agents added to the polymer precursor. The mechanical properties of a polymer may therefore be adapted to a particular use by choice of appropriate materials. For example, the elasticity of a polymer produced from the polymer precursor of the present invention may be increased by incorporation of long chain polyester or polyether segments. The polymer precursors of the present invention may be used in the production of solid molded products, adhesives, foam plastics or coatings for various types of substrates. The polymer precursors of the present invention are blocked polyisocyanates and do not release any volatile blocking agents in use.

Having thus described our invention, the following examples are given by way of illustration. All percentages are given as percentages by weight unless otherwise indicated.

EXAMPLES

Example 1

An isocyanate prepolymer having an isocyanate content of 3.4% was prepared by reacting 2,4-diisocyanatotoluene with a polypropylene glycol having an average molecular weight of 2000. 50 g of this isocyanate prepolymer were vigorously mixed with 3 g of 5-aminobenzoxazolin-2-one (NCO/NH$_2$ equivalent ratio=2:1) and heated at 80° C. for 15 minutes. A reaction product having free isocyanate groups and benzoxazolin-2-one rings was obtained. The product was converted to an elastic polymer by curing at 140° C. for 4 hours.

Example 2

A semi-prepolymer having an isocyanate content of 13.7% was prepared by reacting 1250 g of 4,4'-diisocyanatodiphenylmethane with 56.5 g of butane-1,3-diol. 40.6 g of this semi-prepolymer and 960 g of a trifunctional polyether polyol having a molecular weight of 4800 (obtained by the propoxylation of trimethylolpropane) were mixed with 10 g of 4-aminobenzoxazolin-2-one (NCO/NH$_2$ equivalent ratio=2:1) and heated at 70° C. for 15 minutes. The reaction product (i.e. polymer precursor) contained free isocyanate groups and oxazolin-2-one rings. This polymer precursor was converted into a hard polymer having a Shore hardness of D 42 by curing at 130° C. for 9 hours.

Example 3

A semi-prepolymer having an isocyanate content of 12.3% was prepared by reacting 1250 g of 4,4'-diisocyanatodiphenylmethane with 136 g of trimethyl-hexane-1,6-diol. 45.2 g of this semi-prepolymer and 960 g of the polyether polyol mentioned in Example 2 were mixed with 10 g of 4-aminobenzoxazolin-2-one (NCO/NH$_2$ equivalent ratio=2:1) and heated at 70° C. for 15 minutes. The polymer precursor thus produced contained free isocyanate groups and oxazolin-2-one rings. This polymer precursor was converted into a hard polymer having a Shore hardness D 45 by heating at 130° C. for 2 hours.

Example 4

A semi-prepolymer having an isocyanate content of 13.3% was prepared by reacting 1250 g of 4,4'-diisocyanatodiphenylmethane with 88 g of neopentyl glycol. 42 g of this semi-prepolymer and 960 g of the polyether polyol from Example 2 were mixed with 10 g of 4-aminobenzoxazolin-2-one (NCO/NH$_2$ equivalent ratio=2:1) and heated at 70° C. for 15 minutes. The polymer precursor thus produced contained free isocyanate groups and oxazolin-2-one rings. This polymer precursor was converted into a hard polymer having a Shore hardness D 40 by heating at 130° C. for 2 hours.

Example 5

16.8 g of hexamethylene diisocyanate were mixed with 30 g of 5-aminobenzoxazolin-2-one (NCO/NH$_2$ equivalent ratio=1:1) and heated at 70° C. for 20 minutes. The polymer precursor thus obtained was free from isocyanate groups and contained benzoxazolin-2-one rings.

9.3 g of this polymer precursor were mixed with 25 g of an organic diamine containing 2.6% of amino end groups in the presence of 0.1 g of titanium tetrabutylate (equivalent ratio of oxazolin-2-one rings to amino groups=1:1). This mixture was cured by heating at 140° C. for 1 hour to form a highly elastic, tack-free polymer. The diamine used was prepared by hydrolysis of the isocyanate end groups of an isocyanate prepolymer based on hexamethylene diisocyanate and polypropylene glycol having a molecular weight of 1,000.

Example 6

11.6 g of 2,4-diisocyanatotoluene and 20 g of 5-amino benzoxazolin-2-one (NCO/NH$_2$ equivalent ratio=1:1) in dioxane were heated at 100° C. for 240 minutes. A bifunctional polymer precursor free from isocyanate groups and containing oxazolin-2-one rings was obtained. This polymer precursor was converted to an elastic polymer by heating at 140° C. with the diamine from Example 5 at an equivalent ratio of the reactants of 1:1 in the presence of titanium tetrabutylate (as catalyst for a period of 4 hours.

Example 7

30 g of 5-aminobenzoxazolin-2-one (0.2 mol) were dissolved in 300 ml of anhydrous dioxane and 20.2 g (0.2 mol) of triethylamine were added. 18.3 g (0.1 mol) of adipic acid dichloride were then added dropwise to this solution at room temperature over a period of 30 minutes, during which time the temperature rose to 40° C. The reaction mixture was then stirred while the temperature was maintained at 70° C. for 2 hours. 1 liter of water was added and the mixture suction filtered and washed free from chloride by using an additional quantity of water. 36 g (83% wt. of theoretical yield) of a gray product melting above 300° C. and corresponding to the formula:

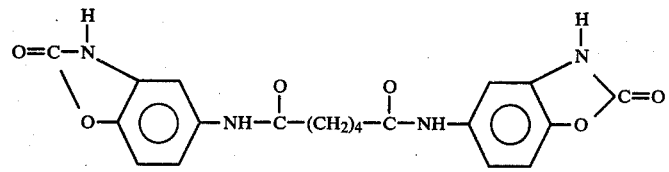

were obtained.

Elemental Analyses: C (observed): 58.0%; (calculated): 58.5%; H (observed): 4.4%; (calculated): 4.4%; N (observed): 12.8%; (calculated): 13.6%.

Example 8

30 g of 6-aminobenzoxazolin-2-one (0.2 mol) were suspended in 200 ml of anhydrous toluene. 0.5 g of triethylene diamine and 16.8 g (0.1 mol) of hexamethylene diisocyanate were then added to the suspension. No free isocyanate was detected after heating at 100° C. for 4 hours. The insoluble solid product was subsequently suction filtered and washed with 200 ml of toluene and 200 ml of petroleum ether. 46 g (98.3 wt. % of the theoretical yield) of a grayish-brown compound melting about 260° C. and corresponding to the structural formula:

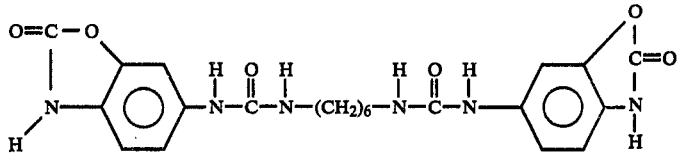

were obtained.

Elemental Analyses: C (observed): 56.9%; (calculated): 56.4%; H (observed): 5.4%; (calculated): 5.2%; N (observed): 16.9%; (calculated): 17.9%.

Example 9

20 g (0.133 mol) of 6-aminobenzoxazolin-2-one were dissolved in 250 ml of anhydrous dioxane. 11.6 g of 2,4-diisocyanatotoluene (0.0665 mol) were then added and the reaction mixture was maintained at 100° C. for 4 hours. No free isocyanate was detected at the end of this time. The insoluble solid product was then suction filtered and washed with 200 ml of petroleum ether. 30 g (95 wt. % of theoretical yield) of a grayish-brown compound soluble in dimethylformamide and melting above 300° C. were obtained. The compound had a structure corresponding to the formula:

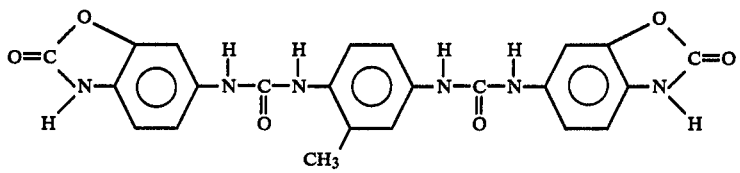

Elemental Analyses: C (observed): 58.6%; (calculated): 59.1%; H (observed): 3.8%; (calculated): 3.7%; N (observed): 16.8%; (calculated): 17.3%.

Example 10

34.8 g (0.2 mol) of 2,4-diisocyanatotoluene were dissolved in 250 ml of anhydrous dioxane. 30 g of 6-aminobenzoxazolin-2-one (0.2 mol) were added dropwise to this solution at 80° C. over a period of 60 minutes. After heating at 80° C. for 4 hours, 50 g (77 wt. % of the theoretical yield) of a sparingly soluble grayish-brown solid having an isocyanate content of 12.4% were obtained.

What is claimed is:

1. A process for the preparation of a polymer precursor containing an oxazolin-2-one ring which forms a high molecular weight polymer upon heating comprising reacting:
   (a) an amino-reactive group containing compound having at least two groups capable of entering into an addition or condensation reaction with primary or secondary aromatically bound amino groups with
   (b) an aromatic amine having
      (i) at least one primary or secondary aromatically-bound amino group and
      (ii) at least one condensed oxazolin-2-one ring in a quantity such that for each aromatically bound primary or secondary amino group there are from 0.95 to 5 groups present in the amino-reactive group containing compound which are capable of reacting with the amino group.

2. The process of claim 1 wherein the amino-reactive group containing compound is an organic polyisocyanate.

3. The process of claim 2 wherein the reactants (a) and (b) are reacted in amounts such that from 0.95 to 2.5 isocyanate groups of the organic polyisocyanate are available for each amino group present.

4. The process of claim 2 wherein the organic polyisocyanate is a polyurethane prepolymer having free isocyanate groups.

5. The process of claim 4 wherein the polyurethane prepolymer is the reaction product of an excess quantity of a simple organic polyisocyanate with an organic polyhydroxyl compound having a molecular weight of from 400 to 10,000.

6. The process of claim 1 wherein the aromatic amine (b) corresponds to the general formula:

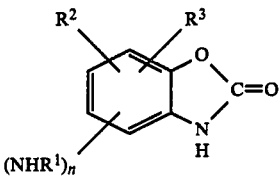

wherein
R¹ represents hydrogen or an aliphatic hydrocarbon group having from 1 to 4 carbon atoms;
R² and R³ (which may be the same or different) represent hydrogen, an aliphatic hydrocarbon group having from 1 to 4 carbon atoms or chlorine, or together represent a condensed benzene ring and
n represents 1.

7. The process of claim 1 wherein the aromatic amine (b) corresponds to the general formula:

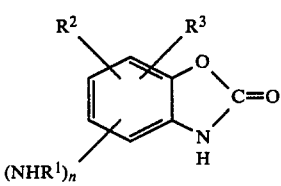

wherein

R¹ represents hydrogen or an aliphatic hydrocarbon group having from 1 to 4 carbon atoms R² and R³ together represent a condensed benzene ring substituted by an amino group NHR¹ n represents 0 or 1.

8. The process of claim 1 wherein the aromatic amine (b) corresponds to the general formula:

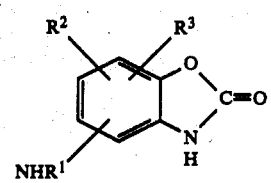

in which:

R¹ represents hydrogen or an aliphatic hydrocarbon group having from 1 to 4 carbon atoms;

R² represents hydrogen, an aliphatic hydrocarbon group having from 1 to 4 carbon atoms or chlorine;

R³ represents a group corresponding to the general formula:

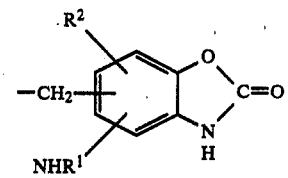

in which R¹ and R² are as defined above.

9. A process for the production of high molecular weight polymers comprising heating to a temperature of from 100° to 200° C. a polymer precursor containing an oxazolin-2-one ring which precursor is the reaction product of
(a) an amino-reactive group containing compound having at least two groups capable of entering into an addition or condensation reaction with primary or secondary aromatically-bound amino groups and
(b) an aromatic amine having (i) at least one primary or secondary aromatically-bound amino group and (ii) at least one condensed oxazolin-2-one ring,
in which from 0.95 to 5 groups capable of reacting with the amino group of (b) were present in the compound (a).

10. The process of claim 9 wherein the heating of the polymer precursor is carried out in the presence of a compound having at least two reactive grous capable of undergoing an addition or condensation reaction with an oxazolin-2-one ring.

11. The process of claim 10 wherein the compound having at least two reactive groups is selected from the group consisting of polyisocyanates and organic polyamines which polyamines have primary and/or secondary amino groups.

* * * * *